United States Patent
Narumi et al.

(10) Patent No.: US 6,770,476 B2
(45) Date of Patent: Aug. 3, 2004

(54) RADIATION RESISTANT BACTERIUM/E. COLI SHUTTLE VECTOR

(75) Inventors: Issay Narumi, Gunma (JP); Zhenli Tu, Gunma (JP); Katsuya Satoh, Gunma (JP)

(73) Assignee: Japan Atomic Energy Research Institute, Tokyo (JP)

( * ) Notice: Subject to any disclaimer, the term of this patent is extended or adjusted under 35 U.S.C. 154(b) by 0 days.

(21) Appl. No.: 10/303,812

(22) Filed: Nov. 26, 2002

(65) Prior Publication Data

US 2003/0175977 A1 Sep. 18, 2003

(30) Foreign Application Priority Data

Feb. 22, 2002 (JP) ........................................ 2002-046377

(51) Int. Cl.[7] .................... C12N 15/00; C12N 15/09; C12N 15/63; C12N 15/70; C12N 15/74
(52) U.S. Cl. .................... 435/320.1; 435/471; 536/23.1
(58) Field of Search .............................. 435/320.1, 471; 536/23.1; 436/471

(56) References Cited

PUBLICATIONS

Mackay et al. The plasmids of Deinococus spp. and the cloning and restriction mapping of plasmid pUE1 Archives of Microbiology vol. 141 pp91–94 1985 (IDS).*

Lange et al., "Engineering a Recombinant Deinococcus radiodurans For Organopollutant Degradation in Radioactive Mixed Waste Environments", Nature Biotechnology, vol. 16, pp. 929–933 (Oct. 1998).

Brim et al., "Engineering Deinococcus radiodurans For Metal Remediation In Radioactive Mixed Waste Environments", Nature Biotechnology, vol. 18, pp. 85–90 (Jan. 2000).

Rob Meime et al., "Characterization of the Minimal Replicon of a Cryptic Deinococcus radiodurans SARK Plasmid and Development of Versatile Escherichia coli–D, radiodurans Shuttle Vectors" Applied and Environmental Microbiology, pp. 3856–3867, vol. 66, No. 9, (Sep. 2000).

Martin W. Mackay, et al., "The Plasmids of Deinococcus ssp. and the Cloning and Restriction Mapping of the D. Radiophilus Plasmid pUE1", Archives of Microbiology, vol. 141, pp. 91–94 (1985).

* cited by examiner

Primary Examiner—James Ketter
Assistant Examiner—Konstantina Katcheves
(74) Attorney, Agent, or Firm—Banner & Witcoff, Ltd.

(57) ABSTRACT

The endogenous plasmid pUE30 from radioresistant bacterium *D. radiopugnans* strain ATCC19172 or a derivative thereof is used as a vector that can autonomously replicate in bacteria of the genus Deinococcus. It may be used to construct a shuttle vector that also contains a plasmid capable of autonomous replication in *E. coli* or a derivative thereof and which can replicate in both a bacterium of the genus Deinococcus and *E. coli*.

11 Claims, 8 Drawing Sheets

SEQUENCE LISTING

<160> NUMBER OF SEQ ID NOS: 7

<210> SEQ ID NO 1
<211> LENGTH: 2467
<212> TYPE: DNA
<213> ORGANISM: Deinococcus radiopugnans
<220> FEATURE:
<221> NAME/KEY: misc_feature
<222> LOCATION: (1)..(2467)
<223> OTHER INFORMATION: Nucleotide sequence of cryptic plasmid pUE30
      from Deinococcus radiopugnans ATCC19172.

<400> SEQUENCE: 1

```
catatgaccg catgaggaca tctgttaata gcgtaaaaat ctctctgctc taatgacatt      60
tagggcagag aaactataga aaacttattc ggttttttctt gcagaagaga ttagaactag    120
tccgccgccc actatacata acagagctaa ggcgtttatt agaaagttgg gggacagaat    180
ttcgtaattg aaacttattt tactagtaat cagttctatt tttttattaa acagatttat    240
tctctcaact attataattc ctataccgaa gagtacgaag atggatgcca agagcatagt    300
cattactccc ttttgcattg tcgctccttt caaatcgtat gatacagtgt tctgacgcgg    360
gtaaaatttt ggtttcacca ctcacgcact tttggaggcc cgatcatgtc tgagggtgaa    420
caatatgaaa gggagtgacg tgctgctgtg cctgtcgctt gaggaacagc agcaggatga    480
aatccatgat cggctgacca gacgcggaca cctgtcggac tcgtcgtctt tgcgtaaggc    540
cctggatcgg ctcatcactg ctggattagt ggtcacgagg aggactgaga atcgggagcg    600
```

-continued

```
cttctactgg ttggcggagg gcgaggccgt cgaagtggcc ttaaatgaag catgggccaa      660
ggctgaggcg gagcgaaacc gggctaggta ggccaaatcc tgaccgtgcc aaagcccag      720 caaaaacagg aattgggtgc cgattttctg cgggtgctgg ggtgttacgc aagattagca     780
ctaaagtgca tcttgcctct gaaactgcgt tccagagggg aaaaaaccag ggtgctgtta     840 atttaatta ctggtcaact tttgggccgt ttttcgaggg gtcaatgcgc gagaaatggc      900
ccaaaaaatc agcagggagg gaggtgctgg acctgccgtt caccccaact ggcaacaccc    960
cgctgggagg cggggtgcta aggtaattct cgaagccagt caaaagtgtc tccaaacacc    1020
gttgattgag ccatcccact ccgaaggacc acttccgatg aacaatcaaa agcaggacag    1080
ctataccgat agggtacggc aaatcgcccc cgtagttcca ctcctggacc tcattgttaa    1140
gcccctcatc cctgaacgag cagccccta tccctatctg gagatgggcc tagccgccct    1200
gcgtggcgag ccggtggaca cccgccgcgc ccaggtgcag cccagcaagc agttccagaa   1260
ggccagccgc ccagcccag ccgccccccc ccttgtgctg acctcagacc agggcgagga    1320
ccaggaggcc gccatgctgc tgcccgagat cgtcgaagag acgcgccgcc gcctggagaa    1380
gcaggcccgc gagaaccgcg agacgcgccg cgccgaacag cgcgcccgct ttcaccagct    1440
cgtgaccgcc ccaccgacg aggccgcgcc ggacttcgtg ccgcctgtga gccttcagga    1500
aggccgtcag cccccagcg gcagtgtgcg cgtcaccttg cccgccctg aagtccctgg     1560 gcctgcctgg ggcgagctga gcgccgacgc ggtgcttgat tcggtgccgt ggctgagcaa    1620 gggcgcgcg ctggtgttcc gcatcatgca catgctggct gtggcgaagg cccaggactg    1680
ccggtatccg gtgatcccca actcggcggc cttccacacg ccccaactgt tgctggcctt    1740
cgtggcgcgt tacaccaccc ggcacttccg gcgactgacc aatgagctgg agcacgctgg    1800
ggtgattgac ggcggcgcgc acgccgcgaa ggtcaagacc ggcatcggca ccacccggca    1860
cctgtgggac ggctcgatct gggcggtcaa gctacggccc agcacctgtg acgcctacct    1920
gtcccccgag gactggcagc acgagtggcg agacttccag gcggacttgg agtcgggcag    1980
gacggcgaaa aagctaatgt cctatctaaa cacctgtgag ggtttagcca ggcaggagca    2040
cgtcctgaaa acctgggccg ttaatcccaa tgcgaaaatg acttcgttgt gtttagagcg    2100
gacatttcag gccgagcaga aaatgaccct ccaggacacg gtttatgccc tgccgctgat    2160
cggggaactg agcgaactca agcaggccgg agccatcgga aacgcggcgt cgatcatctc    2220
gcacgccctg ggcgacagcc acagccgaag attctggtgt gggttgctgt gggcagccac    2280
ccggaacggc tctttagagg cgttctcggc ccagttgctg cggttgctgg cggatgtgca    2340
ggagtccagc gagctgagaa accccggcgc gctgttcgcg gcccgccttc gcagcgcctg    2400
accttcgggg accgcgcccg aagaccaggc gctgctcagt tgggcttgag ggtgattacg    2460
ttctgag                                                              2467
```

<210> SEQ ID NO 2
<211> LENGTH: 31
<212> TYPE: DNA
<213> ORGANISM: Artificial
<220> FEATURE:
<223> OTHER INFORMATION: Sense primer for amplifying pUE30

<400> SEQUENCE: 2
cgcggtacca tcttgcctct gaaactgcgt t                                    31

<210> SEQ ID NO 3
<211> LENGTH: 31

```
<212> TYPE: DNA
<213> ORGANISM: Artificial
<220> FEATURE:
<223> OTHER INFORMATION: Antisense primer for amplifying pUE30

<400> SEQUENCE: 3
gcgggtaccg cactttagtg ctaatcttgc g                              31

<210> SEQ ID NO 4
<211> LENGTH: 30
<212> TYPE: DNA
<213> ORGANISM: Artificial
<220> FEATURE:
<223> OTHER INFORMATION: Sense primer for amplifying pUE30

<400> SEQUENCE: 4
gaaaccgggc taggtacccc aaatcctgac                                30

<210> SEQ ID NO 5
<211> LENGTH: 29
<212> TYPE: DNA
<213> ORGANISM: Artificial
<220> FEATURE:
<223> OTHER INFORMATION: Antisense primer for amplifying pUE30

<400> SEQUENCE: 5
ggtggtaccc tcagacatga tcgggcctc                                 29

<210> SEQ ID NO 6
<211> LENGTH: 24
<212> TYPE: DNA
<213> ORGANISM: Artificial
<220> FEATURE:
<223> OTHER INFORMATION: Sense primer for amplifying Deinococcus
      radiodurans groEL promoter region

<400> SEQUENCE: 6
ttgtcagctt cggtcagttg acat                                      24

<210> SEQ ID NO 7
<211> LENGTH: 20
<212> TYPE: DNA
<213> ORGANISM: Artificial
<220> FEATURE:
<223> OTHER INFORMATION: Antisense primer for amplifying Deinococcus
      radiodurans groEL promoter region

<400> SEQUENCE: 7
tggggtcctc ctgtgagtga                                           20
```

RADIATION RESISTANT BACTERIUM/*E. COLI* SHUTTLE VECTOR

BACKGROUND OF THE INVENTION

This application is based upon and claims the benefit of priority from Japanese Patent Application No. 2002-46377, filed Feb. 22, 2002, the entire contents of this application are incorporated herein by reference.

This invention relates to a novel vector capable of replication in cells of bacteria of the genus Deinococcus, a novel shuttle vector capable of replication in cells of both a bacterium of the genus Deinococcus and *E. coli*, a shuttle vector incorporating the novel shuttle vector, and transformants obtained by introducing those shuttle vectors into bacteria of the genus Deinococcus.

Although the radioresistance of organisms varies greatly with their species, a group of microorganisms having resistance to radiation are known to exist and they are collectively referred to as radioresistant bacteria. Bacteria of the genus Deinococcus are known as representative radioresistant bacteria and to date seven species have been identified (*D. radiodurans, D. radiopugnans, D. radiophilus, D. grandis, D. proteolyticus, D. geothermalis* and *D. murrayi*) (Ferreira et al., Int. J. Syst. Bacteriol., 47:939–947, 1997). It is also known that the radioresistance of those microorganisms is at least about 100 times the resistance of *E. coli* and at least 1000 times that of human cells. If foreign genes that are used to remove difficult-to-decompose substances, toxic substances, etc. could be introduced into these radioresistant bacteria by genetic engineering techniques, it would be possible to use the transformed bacteria to remove difficult-to-decompose substances, toxic substances, etc. that are contained in wastes contaminated by radioactive substances.

Two cases have heretofore been known as examples of incorporating a foreign gene into a bacterium of the genus Deinococcus and expressing a heterologous protein; in one case, toluene dioxygenase was expressed in *D. radiodurans* and difficult-to-dissolve toluene was converted to a substance that was less difficult to dissolve (Lange et al., Nature Biotechnol., 16: 929–933, 1998); in the other case, mercuric (II) ion reductase was expressed in *D. radiodurans* and mercuric ion, Hg(II) ion was reduced to less toxic volatile metallic mercury (Brim et al., Nature Biotechnol., 18: 85–90, 2000). However, in no case have bacteria of the genus Deinococcus other than *D. radiodurans* been transformed with a plasmid vector containing a foreign gene. Furthermore, in the reported cases of transformant preparation, integration-type plasmids which cannot autonomously replicate in bacteria of the genus Deinococcus are used, so there have been several defects such as the inability to control copy number, the small amount of a protein that can be expressed and the need to add an antibiotic to the culture media.

With a view to overcoming these defects, pRAD1, a *D. radiodurans*/*E. coli* shuttle vector, was developed using a replicon of plasmid pUE10 from *D. radiodurans* Sark strain and an *E. coli* vector pMTL23 (Meima and Lidstrom, Appl. Environ. Microbiol., 66: 3856–3867, 2000). However, there has been no report of using pRAD1 to transform other bacteria of the genus Deinococcus than *D. radiodurans*. In addition, pRAD1 which has low segregational stability can be stably replicated in a selective medium containing an antibiotic chloramphenicol but in a non-selective medium that does not contain chloramphenicol, the frequency of appearance of a pRAD1 containing bacterium cannot be maintained at high level and hence such bacterium cannot exist stably. This defect is particularly significant when a radioresistant bacterium into which a foreign gene has been introduced is released into an outside open-air system. For it is extremely difficult to maintain a constant antibiotic level in environments such as soil or liquid wastes contaminated with radioactive substances in order to ensure that the frequency of appearance of the pRAD1 containing bacterium is maintained at high level; what is more, the release of antibiotics into the open-air might increase the possibility of the appearance of an unwanted antibiotic-resistant bacterium, thus eventually polluting the environment.

SUMMARY OF THE INVENTION

An object, therefore, of the invention is to provide a novel vector that is useful in transforming bacteria of the genus Deinococcus and which can stably exist in bacteria of the genus Deinococcus under conditions that have no selective pressure such as antibiotics. Another object of the invention is to provide a novel shuttle vector that can replicate in both a bacterium of the genus Deinococcus and *E. coli* and which can stably exist under conditions that have no selective pressure such as antibiotics.

The present inventors made intensive studies with a view to attaining the stated objects and found that the first object could be attained by using pUE30, an endogenous plasmid from radioresistant bacterium *D. radiopugnans*, or a derivative thereof.

Thus, the first object of the invention can be attained by providing a plasmid capable of autonomous replication in bacteria of the genus Deinococcus, which is the endogenous plasmid pUE30 from *D. radiopugnans* strain ATCC19172 or a derivative thereof.

The present invention attains its second object by providing a shuttle vector that contains both the endogenous plasmid pUE30 from *D. radiopugnans* strain ATCC19172 or a derivative thereof and a plasmid capable of autonomous replication in *E. coli* or a derivative thereof and which can replicate in both a bacterium of the genus Deinococcus and *E. coli*.

DETAILED DESCRIPTION OF THE INVENTION

In its first aspect, the present invention provides a plasmid capable of autonomous replication in bacteria of the genus Deinococcus, which is the endogenous plasmid pUE30 from *D. radiopugnans* or a derivative thereof.

Examples of radioresistant bacterium *D. radiopugnans* that can be used in the invention include *D. radiopugnans* strains ATCC19172 and DSM12027. In the invention, *D. radiopugnans* strain ATCC19172 is preferably used. *D. radiopugnans* strain ATCC19172 can be obtained from the American Type Culture Collection (P.O. Box 1549, Manassas, Va. 20108, USA).

The plasmids of the invention are endogenous plasmids from radioresistant bacterium *D. radiopugnans* and in the case of strain ATCC 19172, pUE30 and pUE31 may be mentioned as examples. In the invention, pUE30 is preferably used. To obtain the plasmid pUE30, *D. radiopugnans* strain ATCC19172 is first cultivated and the obtained cells may be treated by a known method of plasmid preparation, for example, the method described in Sambrook and Russel (Molecular Cloning: A Laboratory Manual, $3^{rd}$ editition (2001)). The nucleotide sequence of pUE30 is depicted as SEQ ID NO:1. Although pUE30 is a double-stranded circular DNA, the nucleotide sequence depicted as SEQ ID NO:1 shows the restriction enzyme NdeI recognition site of pUE30 as 5' terminus.

In addition to pUE30 having the nucleotide sequence depicted as SEQ ID NO:1, the present invention includes plasmids that are derivatives of pUE30 and which can autonomously replicate in bacteria of the genus Deinococcus. When used in the invention, "derivative" of a plasmid means plasmid that involves any modification(s) of the plasmid and which at least contains a region involved in replication. Exemplary modifications include, but are not limited to, one or more nucleotide mutations in the DNA sequence of the plasmid (e.g. deletion, substitution and addition) and modifications that do not contain a specified region of DNA sequence of the plasmid. Exemplary derivatives of pUE30 include, but are not limited to, those derivatives which only contain a region that in effect is involved in the replication of pUE30, more specifically, fragments starting with nucleotide 693 and ending with nucleotide 417 in pUE30 depicted as SEQ ID NO:1 (nucleotides 693-2467-1-417), as well as pUE30 or a portion thereof that have other DNA sequences inserted thereinto.

The thus prepared plasmids are capable of autonomous replication not only in the radioresistant bacterium *D. radiopugnans* which is their origin but also in a wide range of other bacteria of the genus Deinococcus.

In its second aspect, the present invention provides a shuttle vector that can autonomously replicate in both a bacterium of the genus Deinococcus and a bacterium of another genus. More specifically, the invention provides a shuttle vector that contains both the endogenous plasmid pUE30 from *D. radiopugnans* or a derivative thereof and a plasmid capable of autonomous replication in *E. coli* or a derivative thereof and which can replicate in both a bacterium of the genus Deinococcus and *E. coli*.

In the technical field of the invention, a shuttle vector generally means a vector that contains the DNA replication mechanisms of two organisms, optionally further containing a selection marker, and which can autonomously replicate in the cell of either of the two organisms. Therefore, in the present invention, a shuttle vector capable of autonomous replication in both a bacterium of the genus Deinococcus and a bacterium of another genus can be constructed by linking a DNA replication mechanism that functions in a bacterium of the genus Deinococcus and a DNA replication mechanism that functions in a bacterium of another genus. As such DNA replication mechanisms, the whole of a plasmid having the ability to replicate autonomously or a derivative thereof having the ability to replicate; bacteria other than those of the genus Deinococcus include *E. coli*.

Examples of the DNA replication mechanism that functions in bacteria of the genus Deinococcus and which is used to construct the Deinococcus bacterium/*E. coli* shuttle vector of the invention include the sequences from the endogenous plasmids pUE30 and pUE31, both derived from *D. radiopugnans*, as well as the sequence of an endogenous plasmid pUE1 derived from *D. radiophilus*. Preferably, the endogenous plasmid pUE30 from *D. radiopugnans* and derivatives thereof are used.

The plasmid pUE30 to be used in constructing the shuttle vector of the invention may employ all or part of the nucleotide sequence depicted as SEQ ID NO:1. If part of the nucleotide sequence depicted as SEQ ID NO:1 is to be used, it must contain at least a region involved in the replication of pUE30 but the region that is not necessary for its replication may be eliminated. Considering the case of using the shuttle vector incorporating a useful foreign gene, the size of the shuttle vector is desirably made minimum, except for region(s) other than that involved in replication. A fragment of pUE30 that is obtained by cutting with a restriction enzyme may be ligated to a plasmid capable of autonomous replication in *E. coli* and a bacterium of the genus Deinococcus is transformed with the obtained recombinant plasmid and the region necessary for replication can be determined by confirming that the aforementioned recombinant plasmid is retained in the transformed bacterium of the genus Deinococcus. If there is no suitable restriction site, a new restriction site may be introduced at a specified site by using a technique of site-directed mutagenesis that is known in the technical field of the present invention. Alternatively, synthetic DNA containing part of the nucleotide sequence depicted as SEQ ID NO:1 may be used as a primer in PCR which is performed, with pUE30 used as a template, to amplify partial fragments of pUE30, which are subsequently used for ligation to a plasmid capable of replication in a bacterium of another genus. Examples of such synthetic DNA primer include synthetic DNA having the nucleotide sequences depicted as SEQ ID NO:2 and SEQ ID NO:3, as well as synthetic DNA having the nucleotide sequences depicted as SEQ ID NO:4 and SEQ ID NO:5.

Examples of the DNA replication mechanism that functions in *E. coli* and which may be used to construct the shuttle vector of the invention include, but are not limited to, any of the plasmid vectors that are commonly used in the technical field of the invention. Specific examples include pUC18, pUC19, pHSG298, pHSG299, pBR322, pSC101 and pGBM5. These plasmid vectors can be purchased on the market; they are also available to anyone skilled in the art from the collection of cloning vectors at the National Institute of Genetics (1111, Yata, Mishima, Shizuoka, 411–8540, Japan). Again, these plasmids may be used either in their entirely or in part. If they are to be used in part, a region involved in plasmid replication in *E. coli* must be contained but regions that are not necessary for replication may be eliminated.

The plasmid and the shuttle vector of the invention may optionally contain a selection marker gene. Selection marker genes that can be used are genes conferring resistance to antibiotics such as ampicillin, kanamycin, chloramphenicol, tetracycline, hygromycin and spectinomycin. These antibiotic resistance genes are typically contained in the above-listed *E. coli* plasmid vectors; for example, pUC18 has an ampicillin resistance gene and pHSG298 has a kanamycin resistance gene. These antibiotic resistance genes can be used to construct the shuttle vector together with the region necessary for replication.

If a promoter sequence that functions in bacteria of the genus Deinococcus is ligated upstream of those selection marker genes, the latter can be allowed to function as marker genes when transformants of bacteria of the genus Deinococcus are to be acquired by introducing the shuttle vector. Examples of the promoter sequence that functions in bacteria of the genus Deinococcus include known promoter sequences that are described in Smith et al. (Plasmid, 22: 132–142, 1989), Funayama et al. (Mutat. Res., 435: 151–161, 1999) and Meima et al. (J. Bacteriol. 183: 3169–3175, 2001). If it can be verified that the shuttle vector exists stably in the obtained transformants of bacteria of the genus Deinococcus even if they are in an antibiotic-free environment, there is no need to add antibiotics for subsequent cultivation of those transformants.

By further incorporating a reporter gene into the above shuttle vector, another shuttle vector can be constructed. It is known in the technical field of the invention that a luciferase gene, lacZ gene, cat gene, etc. can be used as the reporter gene. In the invention, lux which is a luciferase gene from the host DNA of the North American firefly, *Photinus pyralis*, may be used as the luciferase gene. The reporter gene can be incorporated into the shuttle vector at a suitable restriction site. If there is no suitable restriction site, a multiple cloning site from an *E. coli* plasmid vector may be inserted into the shuttle vector. The Deinococcus bacterium/ *E. coli* shuttle vector of the invention has a multiple cloning site from an *E. coli* plasmid vector inserted therein either entirely or in part, so a luciferase gene (or other foreign gene) can be inserted into that shuttle vector using suitable restriction enzymes. If the reporter gene (or other foreign gene) is not effectively expressed in bacteria of the genus Deinococcus, the above-mentioned promoter sequence which functions in bacteria of the genus Deinococcus may be ligated upstream of the gene to be expressed.

The thus prepared shuttle vectors of the invention can be produced in large amounts using *E. coli* capable of fast growth. Examples of methods for transforming *E. coli* using the shuttle vectors of the invention are described in detail in Sambrook and Russel (Molecular Cloning: A Laboratory Manual, 3$^{rd}$ edition (2001)). Specific examples include, but are not limited to, the calcium chloride technique and electroporation. In order to obtain transformants by introducing the shuttle vectors of the invention into bacteria of the genus Deinococcus, spontaneous transformation methods using the calcium chloride technique may be employed as described, for example, in Kitayama et al. (J. Bacteriol. 155: 1200–1207, 1983) and Meima et al. (Appl. Environ. Microbiol., 66: 3856–3867, 2000); however, these are not the sole methods that can be used in the invention. Exemplary bacteria of the genus Deinococcus that can be used in the invention as the host into which the shuttle vectors are to be introduced include *D. grandis*, *D. radiodurans* strain ATCC 13939 and *D. radiodurans* strain ATCC 35073 (Sark strain). More preferably, *D. grandis* strain ATCC 43672 is used. *D. grandis* strain ATCC 43672 can be obtained from the above-mentioned American Type Culture Collection.

Examples of the invention are described below. The following examples are provided only for the purpose of describing the invention more specifically and it is by no means intended to limit the scope of the invention by those examples.

EXAMPLE 1

Preparing Plasmids
(1) Isolation and Purification of a Plasmid

*D. radiopugnans* strain ATCC 19172 obtained from the American Type Culture Collection was cultivated in a TGY medium (0.5% tryptone-peptone, 0.3% yeast extract, 0.1% glucose) for 24 hours and centrifuged to collect the cells. Plasmid fractions were extracted from the cells with a QIA filter Plasmid kit (Qiagen) and plasmid isolation and purification were effected by agarose gel electrophoresis. As a result, a plasmid of about 2.5 kb was observed. Mackay et al. (Arch. Microbiol., 141: 91–94, 1985) examined *D. radiopugnans* with an electron microscope and reported the presence of the plasmid pUE30 with a size of about 2.5 kb. Hence, the 2.5-kb plasmid separated and purified in Example 1 was designated pUE30.

(2) Determining the Nucleotide Sequence

A restriction map was prepared for the above purified pUE30 and it was confirmed that pUE30 had one HincII site and one Aor51HI site. In the next place, pUE30 was digested with HincII (New England Biolabs, Inc.) to give a 2.5-kb fragment or digested with Aor51HI (Takara Shuzo) to give a 2.5-kb fragment; either fragment was ligated to a multiple cloning site in *E. coli* vector plasmid pGBM5 obtained from the collection of cloning vectors at the National Institute of Genetics, whereby a plasmid was prepared. Further, the plasmid was processed with a Kilo-sequence Deletion kit (Takara Shuzo) to prepare nested deletion clones that had part of the plasmid deleted progressively. Subsequently, with these nested deletion clones used as templates, the full DNA nucleotide sequence at the site of pUE30 insertion was determined by the dideoxy termination method using a commercial universal primer. The sequencing reaction was performed with a BigDye Terminator Cycle Sequencing kit (Applied Biosystems) and electrophoresis was performed with a DNA Sequencer ABI PRISM 377 (Applied Biosystems). The determined full nucleotide sequence is depicted as SEQ ID NO:1.

A further analysis of the obtained nucleotide sequence showed that pUE30 had 2467 bp in full length, with two open reading frames (ORF), one consisting of 267 nucleotides and the other 1068 nucleotides; they were designated repC and repD, respectively. Protein RepC encoded by repC had 25.8–31.6% amino acid identity with RepC found in the repABC-type plasmid of α-proteobacteria; protein RepD encoded by repD had amino acid identities of 26.6%, 24.6% and 26.8% with RepT of plasmid pTsp45s from Thermus sp. strain YS45, RepA of plasmid pMY1 from Thermus sp. strain ATCC 27737 and RepU of plasmid pUE10 from *D. radiodurans* strain Sark, respectively.

EXAMPLE 2

Constructing Shuttle Vectors
(1) Constructing pZT15

With pUE30 used as a template and synthetic DNA as a primer which had the nucleotide sequences depicted as SEQ ID NO:2 and SEQ ID NO:3, PCR was carried out with an AmpliTaq Gold DNA polymerase (Applied Biosystems), thereby yielding a PCR product that contained the full nucleotide sequence of pUE30 starting at nucleotide 789 and which had a restrictioin enzyme SphI site added at both termini.

Subsequently, plasmid pKatCAT (Funayama et al., Mutat. Res., 435: 151–161, 1999) having a replication origin region of *E. coli* vector pUC19, ampicillin resistance gene capable of functioning in *E. coli* and chloramphenicol resistance gene capable of functioning in *D. radiodurans* was digested with SphI, mixed with an SphI digest of the already obtained PCR product and ligation was effected by DNA ligase (TaKaRa).

Figure 1:
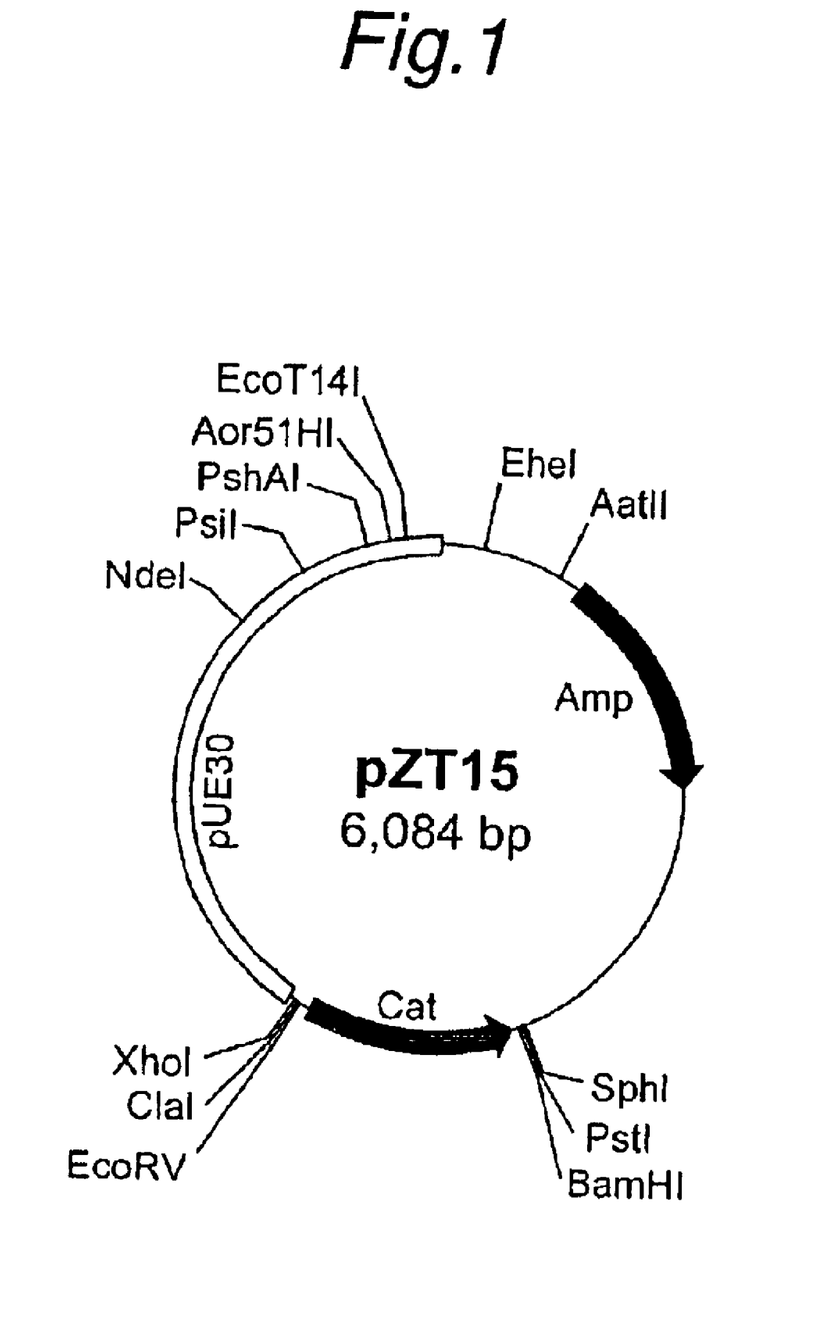
FIG. 1 is a restriction map for the shuttle vector pZT15 of the invention.

The thus prepared plasmid was introduced into *E. coli* strain JM109 by electroporation so as to transform the *E. coli*. From the transformants showing ampicillin resistance, clones having a plasmid (ca. 6.1 kb) in which pUE30 had been ligated to pKatCAT were selected and the plasmid was designated shuttle vector pZT15. The structure of pZT15 is shown in FIG. 1.

(2) Constructing pZT17

With pUE30 used as a template and a synthetic DNA as a primer which had the nucleotide sequences depicted as SEQ ID NO:4 and SEQ ID NO:5, PCR was carried out as in (1), thereby yielding a PCR product that contained a portion of the nucleotide sequence of pUE30 (a fragment of ca. 2.3 kb starting at nucleotide 693 in SEQ ID NO:1 and ending at nucleotide 417; nucleotides 693-2467-1-417) and which had a restriction enzyme SphI site added at both termini.

Figure 2:
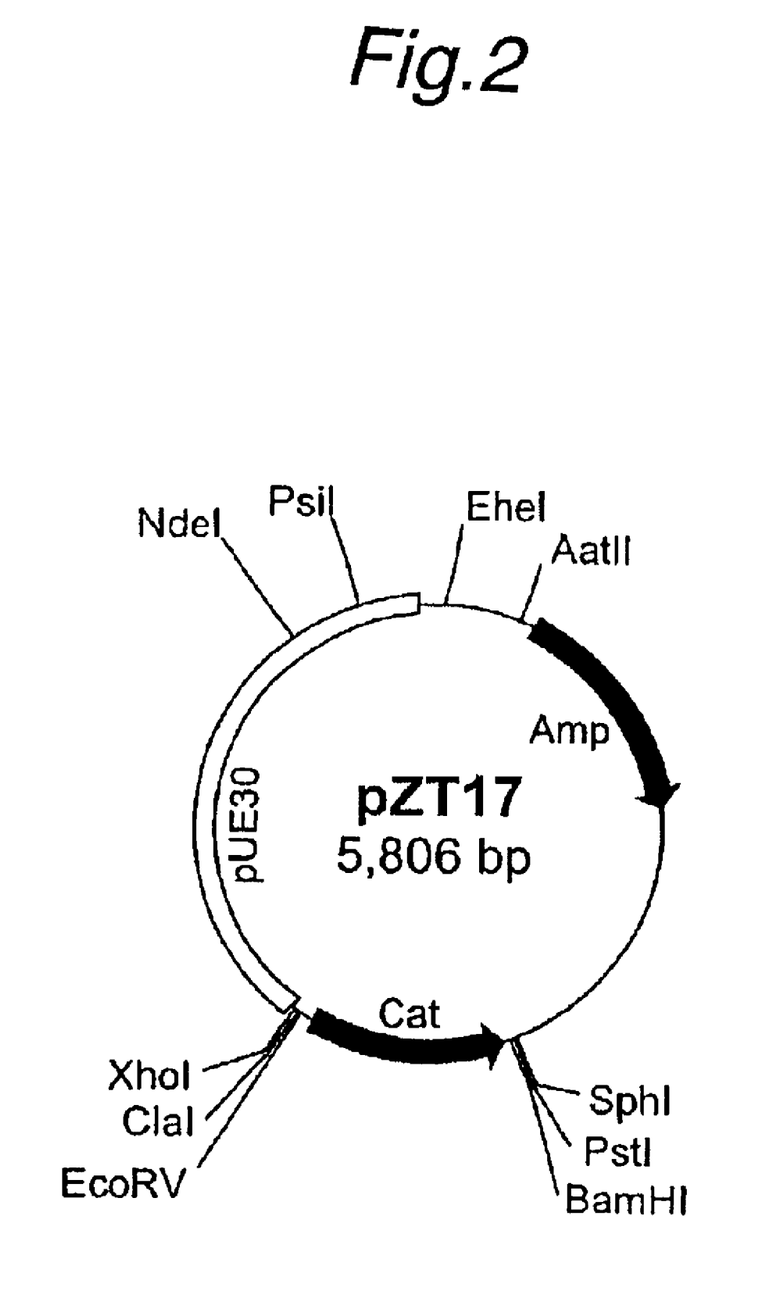
FIG. 2 is a restriction map for the shuttle vector pZT17 of the invention.

Subsequently, the PCR product was ligated to plasmid pKatCAT and used to transform *E. coli* strain JM109 as in (1). From the transformants showing ampicillin resistance, clones having a plasmid (ca. 5.8 kb) in which a portion of pUE30 had been ligated to pKatCAT were selected and the plasmid was designated shuttle vector pZT17. The structure of pZT17 is shown in FIG. 2.

(3) Transformation of Bacteria of the Genus Deinococcus with Shuttle Vectors

*D. grandis* strain ATCC 43672 and *D. radiodurans* strain ATCC 13939 was transformed with the above-described shuttle vector pZT15 or pZT17. Transformation was performed by the calcium chloride technique in accordance with the method of Kitayama et al. (J. Bacteriol., 155: 1200–1207, 1983). Whether the shuttle vector was pZT15 or pZT17, chloramphefical resistant clones were obtained. From these cells, plasmid fractions were extracted with a QIAprep Miniprep Plasmid kit (Qiagen) and analyzed by agarose gel electrophoresis to see whether the introduced plasmids were retained in the transformants.

Figure 3:
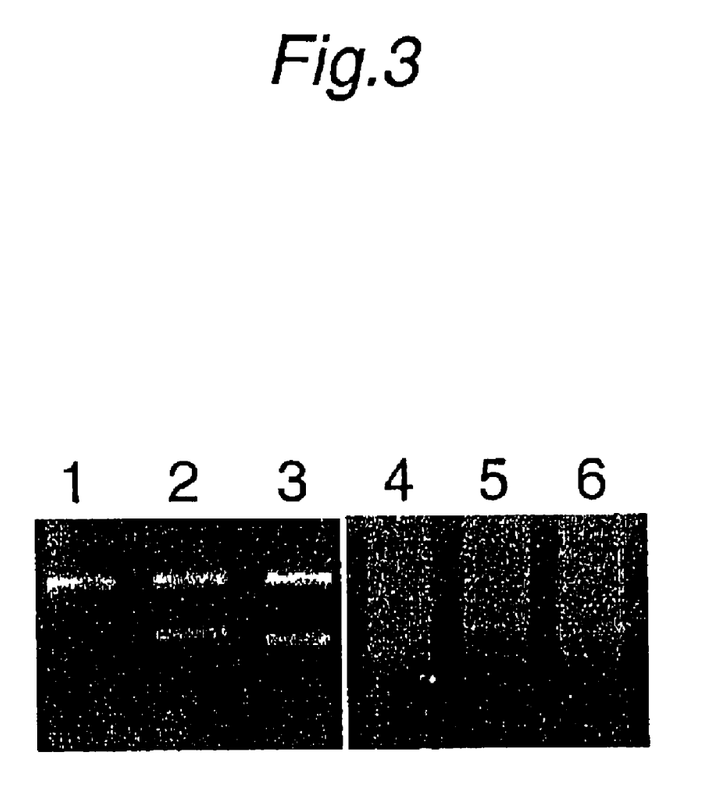
FIG. 3 is an agarose gel electrophoretic image taken to determine whether introduced plasmids were retained in transformants.

The results are shown in FIG. 3, in which lanes 1–3 represent the plasmid from *D. grandis* strain ATCC 43672, lanes 4–6 represent the plasmid from *D. radiodurans* strain ATCC 13939, provided that the plasmids of lanes 1 and 4 derive from the intact bacteria, the plasmids of lanes 2 and 5 derive from the bacteria transformed with pZT15, and the plasmids of lanes 3 and 6 derive from the bacteria transformed with pZT17. The plasmid occurring common to lanes 1–3 is an endogenous plasmid (ca. 8 kb) in *D. grandis* strain ATCC 43672. From these results, it can be seen that both shuttle vectors pZT15 and pZT17 were stably retained in bacteria of the genus Deinococcus.

(4) Stability of Shuttle Vectors in *D. grandis*

*D. grandis* containing pZT15 or pZT17 was cultivated overnight in a TGY medium containing chloramphenicol. Subsequently, the culture solution was diluted 256-fold, inoculated in a chloramphenicol-free TGY medium and cultivated at 30° C. After cell division through 8 generations, the culture solution was again diluted 256-fold, inoculated in a chloramphenicol-free TGY medium and cultivated at 30° C. These procedures were repeated in a non-selective medium to achieve cell division through 40 generations.

For each division through 8 generations, a portion of the culture solution was taken and smeared on both a TGY plate medium and a chloramphenicol-containing TGY plate medium to determine the number of chloramphenicol-resistant cells relative to the total viable cell count in the culture solution. As a control, the Deinococcus/*E. coli* shuttle vector pRAD1 described in Meima and Lidstrom (Appl. Environ. Microbiol., 66: 3856–3867, 2000) was introduced into *D. grandis* and the stability of pRAD1 in the obtained transformants was similarly investigated.

Figure 4:
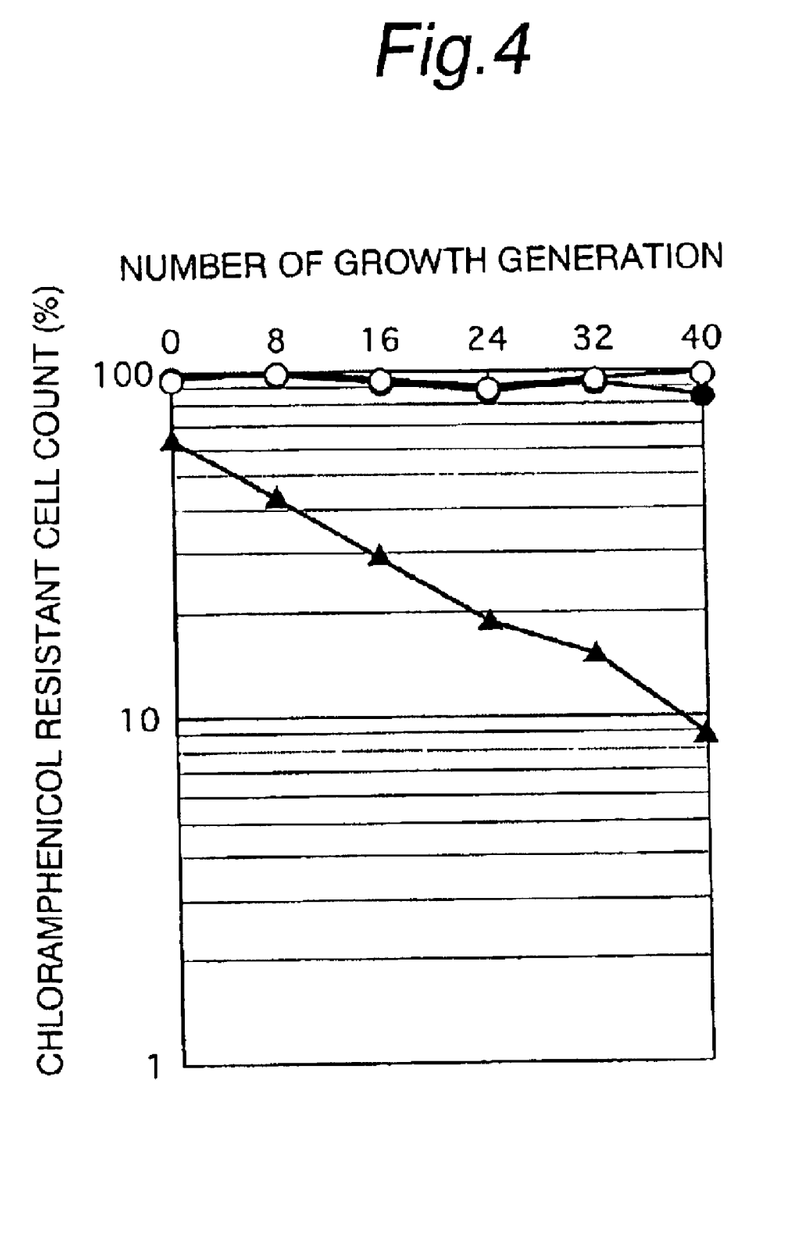
FIG. 4 is a graph showing the result of an investigation for the stability of the shuttle vector in *D. grandis* strain ATCC43672.

The results are shown in FIG. 4; refers to the transformants with pZT15, the transformants with pZT17, and the transformants with pRAD1. The vertical axis of the graph plots the number of chloramphenicol resistant clones relative to the total viable cell count, and the horizontal axis plots the number of growth generations. According to FIG. 4, pRAD1 could not stably exist within *D. grandis* in the non-selective medium but pZT15 and pZT17 were stably retained in *D. grandis* even when it was cultivated in the non-selective medium.

EXAMPLE 3

Constructing Shuttle Vectors having Luciferase Gene (1) Constructing pZTGL2 and pZTGL4

With genomic DNA of *D. radiodurans* strain ATCC 13939 used as a template and synthetic DNAs as a pair of primers which had the nucleotide sequences depicted as SEQ ID NO:6 and SEQ ID NO:7, PCR was carried out using Pfu Turbo DNA polymerase (Stratagene), thereby amplifying the known groEL promoter region (131 bp) described in Meima et al. (J. Bacteriol. 183: 3169–3175, 2001) which could function in *D. radiodurans*. Subsequently, plasmid pSP-lux+ (Promega) containing a luciferase gene was digested with NcoI and the termini of the resulting DNA fragments were made blunt with T4 DNA polymerase (TaKaRa). The separately prepared PCR product was ligated with the blunt-ended pSP-lux+ to produce pGroE-lux+2 and pGroE-lux+4 (both 4,235 bp).

Figure 5:
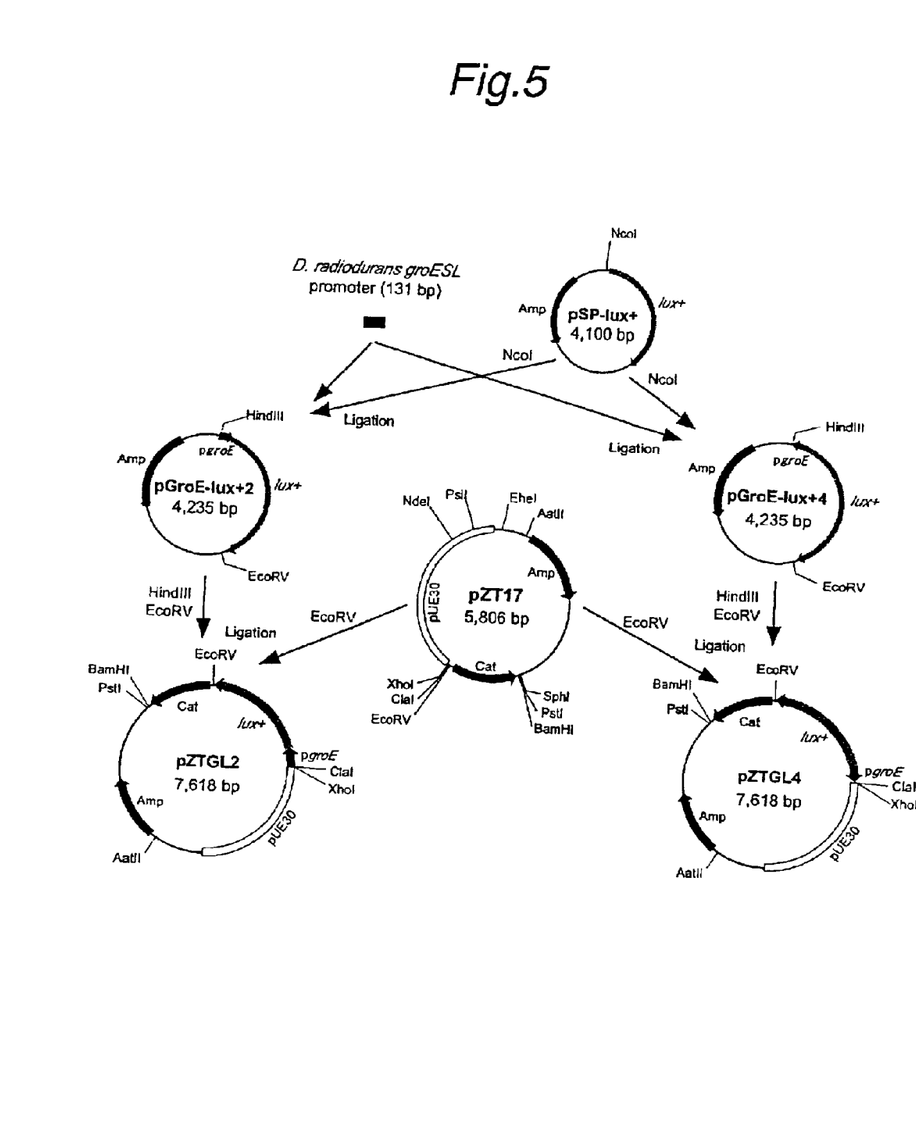
FIG. 5 is a diagram outlining the procedures of constructing the shuttle vectors pZTGL2 and pZTGL4 containing a luciferase gene according to the invention.

These plasmids were digested with HindIII and the cleaved ends were made blunt, followed by digestion with EcoRV to give DNA fragments each containing the groEL promoter and the luciferase gene. Subsequently, these DNA fragments were inserted into the shuttle vector pZT17 at EcoRV site to construct pZTGL2 and pTZGL4 (both 7,618 bp). An outline for the construcion of pZTGL2 and pZTGL4 is shown in FIG. 5. *D. grandis* was transformed with the constructed plasmids to yield chloramphenicol-resistant clones.

(2) Transforming Bacterium of the Genus Deinococcus with Shuttle Vectors

*D. grandis* strain ATCC 43672 was transformed with the above-described shuttle vector pZTGL2 or pZTGL4. As in Example 2(3), transformation was performed by the calcium chloride technique in accordance with the method of Kitayama et al. (J. Bacteriol., 155: 1200–1207, 1983). Whether the shuttle vector was pZTGL2 or pZTGL4, chloramphefical resistant clones were obtained. From these cells, plasmid fractions were extracted with a QIAprep Miniprep Plasmid kit (Qiagen) and analyzed by agarose gel electrophoresis to see whether the introduced plasmids were retained in the transformants.

Figure 6:
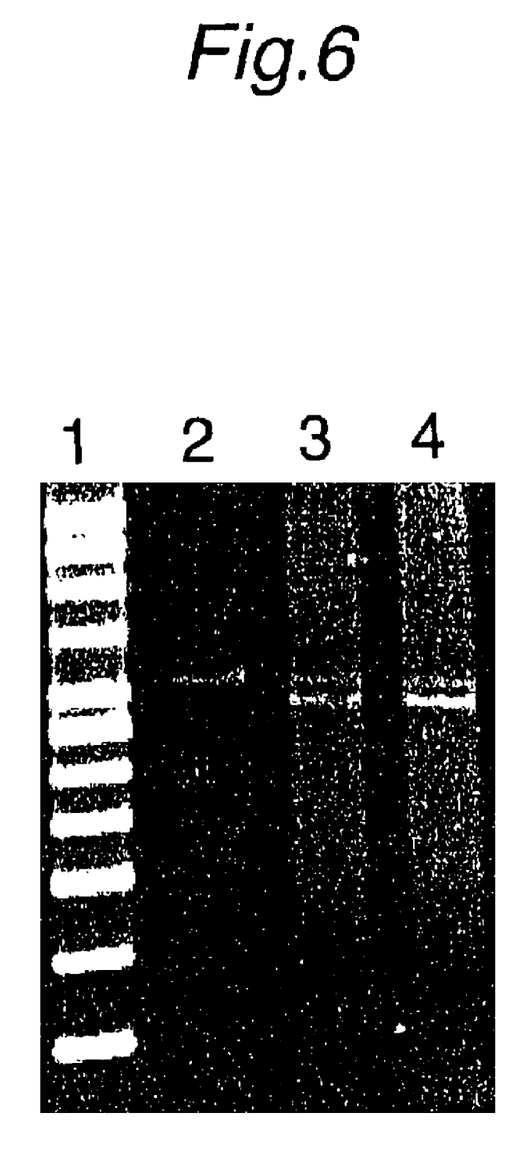
FIG. 6 is an agarose gel electrophoretic image taken to determine whether introduced plasmids were retained in transformants.

The results are shown in FIG. 6, in which lane 2 represents the plasmid from intact *D. grandis* strain ATCC 43672, lane 3 represents the plasmid from *D. grandis* strain ATCC 43462 transformed with pZTGL2, lane 4 represents the plasmid from *D. grandis* strain ATCC 43672 transformed with pZTGL4, and lane 1 represents the marker. The plasmid occurring common to lanes 2–4 is an endogenous plasmid (ca. 8 kb) in *D. grandis* strain ATCC 43672. From these results, it can be seen that both shuttle vectors pZTGL2 and pZTGL4 were stably retained in a bacterium of the genus Deinococcus.

(3) Detecting Luciferase Activity

Figure 7:
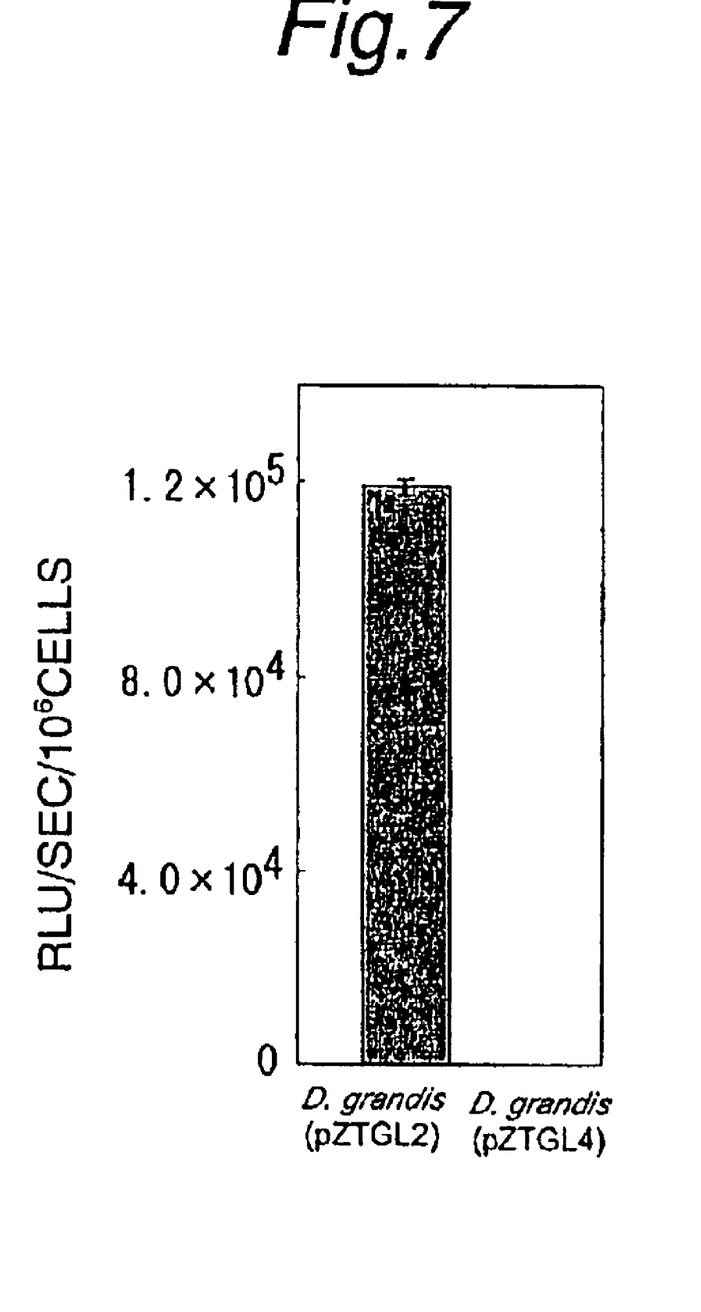
FIG. 7 is a graph showing the result of measurement of luciferase activity in *D. grandis* strain ATCC43672 transformed with pZTGL2 or pZTGL4.

The thus obtained transformants were cultivated in a TGY medium at 30° C. Twenty-four hours later, 10 μl of the culture solution was mixed with an equal volume of Bright-Glo Luciferase Assay Solution (Promega) and, one minute later, the chemiluminescence activity was measured for one minute with Lumi Imager F1 (Roche Molecular Biochemicals). The results of measurement are shown in FIG. 7; the luciferase activity is expressed by RLU (relative light units) per second in $10^6$ cells. It was confirmed that the transformants containing pZTGL2 in which the groEL promoter and the luciferase gene were placed in the normal orientation expressed luciferase whereas the transformants containing pZTGL4 in which the promoter and the luciferase were placed in reverse orientation did not have luciferase activity.

(4) Stability of pZTGL2 in *D. grandis*

*D. grandis* transformed with pZTGL2 was cultivated through 40 generations in a chloramphenicol-free TGY medium by the same procedures as in Example 2(4) to yield sample A. In a different run, the same transformants were cultivated through 40 generations in a chloramphenicol-containing TGY medium to give sample B.

Figure 8:
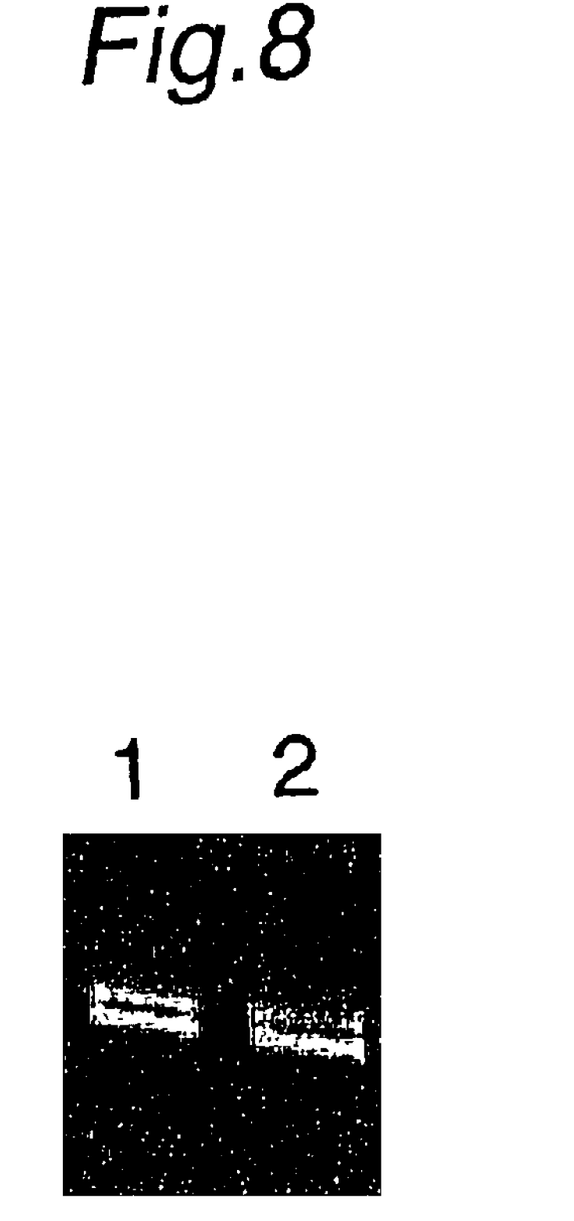
FIG. 8 is an electrophoretic image of a plasmid extracted from *D. grandis* strain ATCC43672 taken to show that the plasmid was stable in *D. grandis* strain ATCC43672 transformed with pZTGL2.

Electrophoretic images of the plasmids extracted from samples A and B are shown in FIG. 8, in which lane 1 represents sample A and lane 2 sample B. In each lane, the upper band represents the endogenous plasmid (size of ca. 8 kb) in *D. grandis* strain ATCC 43672 and the lower band represents pZTGL2 (size of ca. 7.6 kb). The plasmid extracted from sample A had approximately the same copy number as the plasmid extracted from sample B.

Subsequently, samples A and B were measured for luciferase activity by the same procedures as in Example 3(3); the luciferase activity of sample A relative to that of sample B was 85±0.4%. This result shows that the stability of pZTGL2 in *D. grandis* cultivated in the non-selective medium was comparable to that of pZT17 in *D. grandis* shown in FIG. 4. Thus, it was shown that pZT17 as well as pZTGL2 which had a 1.8-kb foreign gene inserted into pZT17 could be stably retained in *D. grandis* when it was cultivated in the non-selective medium.

According to the invention, there are provided novel plasmids from bacteria of the genus Deinococcus, as well as shuttle vectors using such plasmids. The shuttle vectors can autonomously replicate in cells of bacteria of the genus Deinococcus and *E. coli*, so they are useful not only in vector DNA recombinant procedures but also in introducing genes into bacteria of the genus Deinococcus. In particular, they can be applied to remove hard-to-decompose substances and toxic substances from wastes containing radioactive substances, as well to the technology of capturing radioactive heavy metals. The shuttle vectors of the invention are stably retained in a host during cultivation in a non-selective medium, so they can be used in those fields of application irrespective of whether an open-air or closed system is employed. In addition, the shuttle vectors of the invention, if they have a luciferase gene, are useful in monitoring the distribution of transformant growths and their possible effects on the environment.

What is claimed is:

1. A plasmid capable of autonomous replication in bacteria of the genus Deinococcus, wherein the plasmid comprises a fragment of pUE30 derived from *D. radiopugnans* strain ATCC 19172 and wherein the fragment of pUE30 involved in pUE30 replication comprises nucleotides 417–693 of SEQ ID NO:1.

2. The plasmid according to claim 1, which is capable of expressing a foreign gene in a transformed bacterium of the genus Deinococcus.

3. The plasmid according to claim 1, wherein the endogenous plasmid pUE30 has a nucleotide sequence depicted as SEQ ID NO:1.

4. A shuttle vector comprising DNA replication sequences of (1) an endogenous plasmid pUE30 from a radiopugnans strain ATCC 19172 and (2) a plasmid capable of autonomous replication in *E. coli*, wherein the shuttle vector replicates in both a bacterium of the genus Deinococcus and the species *E. coli*, wherein the DNA replication sequence of the endogenous plasmid pUE30 comprises nucleotides 417–693 of SEQ ID NO:1.

5. The shuttle vector according to claim 4, wherein the plasmid capable of autonomous replication in *E. coli* is selected from the group consisting of pUC18, pUC19, pHSG298, pHSG299, pBR322, pSC101 and pGBM5.

6. The shuttle vector according to claim 4, which further contains a luciferase gene.

7. The shuttle vector according claim 4, which is capable of expressing a foreign gene in a transformed bacterium of the genus Deinococcus.

8. A transformant containing the shuttle vector according to claim 4.

9. A transformant containing the shuttle vector according to claim 5.

10. A transformant containing the shuttle vector according to claim 6.

11. A transformant containing the shuttle vector according to claim 7.

* * * * *

UNITED STATES PATENT AND TRADEMARK OFFICE
CERTIFICATE OF CORRECTION

PATENT NO. : 6,770,476 B2
DATED : August 3, 2004
INVENTOR(S) : Issay Narumi et al.

It is certified that error appears in the above-identified patent and that said Letters Patent is hereby corrected as shown below:

Column 13,
Line 66, please replace "a radiorepugnans" with -- *D. radiorepugnans* --

Signed and Sealed this

Fourteenth Day of June, 2005

JON W. DUDAS
*Director of the United States Patent and Trademark Office*